United States Patent
Hu

(10) Patent No.: US 12,127,967 B2
(45) Date of Patent: Oct. 29, 2024

(54) TONGUE STABILIZING ORAL APPLIANCE

(71) Applicant: Jerry Chi Hu, Soldotna, AK (US)

(72) Inventor: Jerry Chi Hu, Soldotna, AK (US)

(73) Assignee: Jerry Chi Hu, DDS Family Dentistry, LLC, Soldotna, AK (US)

( * ) Notice: Subject to any disclaimer, the term of this patent is extended or adjusted under 35 U.S.C. 154(b) by 0 days.

(21) Appl. No.: 18/246,789

(22) PCT Filed: Sep. 17, 2021

(86) PCT No.: PCT/US2021/050914
§ 371 (c)(1),
(2) Date: Mar. 27, 2023

(87) PCT Pub. No.: WO2022/066532
PCT Pub. Date: Mar. 31, 2022

(65) Prior Publication Data
US 2023/0404794 A1    Dec. 21, 2023

Related U.S. Application Data

(60) Provisional application No. 63/084,250, filed on Sep. 28, 2020.

(51) Int. Cl.
*A61F 5/56*    (2006.01)

(52) U.S. Cl.
CPC .................. *A61F 5/566* (2013.01)

(58) Field of Classification Search
CPC .. A61F 5/56; A61F 5/566; A61F 7/008; A61F 2005/563; A61C 7/08; A61C 7/10; A61C 7/36
See application file for complete search history.

(56) References Cited

U.S. PATENT DOCUMENTS

| | | | |
|---|---|---|---|
| 6,877,513 B2 | 4/2005 | Scarberry | |
| 7,607,439 B2* | 10/2009 | Li | A61F 5/566 433/7 |
| 7,954,494 B1 | 6/2011 | Connor | |
| 8,261,748 B1* | 9/2012 | Goldberg | A61B 5/682 433/7 |
| 8,857,439 B2* | 10/2014 | Hegde | A61F 5/566 128/848 |
| 9,504,537 B2* | 11/2016 | Johnson | A61N 5/10 |
| 10,206,809 B1 | 2/2019 | Goldberg | |
| 2007/0289600 A1* | 12/2007 | Li | A61F 5/566 128/860 |

(Continued)

FOREIGN PATENT DOCUMENTS

| | | |
|---|---|---|
| JP | 2005-095218 A | 4/2005 |
| KR | 20-0226262 | 6/2001 |

OTHER PUBLICATIONS

International Search Report for International Application No. PCT/US2021/050914 mailed Jan. 13, 2002 (4 pages).

*Primary Examiner* — Camtu T Nguyen

(57) ABSTRACT

An apparatus for providing tongue stabilization during oral appliance therapy. The tongue stabilization apparatus is configured to hold a user's tongue in place or prohibit it from dropping back posteriorly, thereby stabilizing the user's tongue in a non-obstructive position through sleep, which can help to prevent the user from experiencing obstructive sleep apnea.

20 Claims, 6 Drawing Sheets

(56) References Cited

U.S. PATENT DOCUMENTS

2009/0241969 A1* 10/2009 Walker .................... A61F 5/566
　　　　　　　　　　　　　　　　　　　128/848
2011/0180076 A1*  7/2011 Hegde ..................... A61F 5/566
　　　　　　　　　　　　　　　　　　　128/848
2012/0024297 A1*  2/2012 Hegde ..................... A61F 5/566
　　　　　　　　　　　　　　　　　　　128/848

* cited by examiner

TONGUE STABILIZING ORAL APPLIANCE

CROSS-REFERENCE TO RELATED APPLICATIONS

The present application is a U.S. National Stage of PCT/US2021/050914 filed on Sep. 17, 2021, which claims the benefit of U.S. Provisional Patent Application No. 63/084,250, titled "Tongue Stabilizing Oral Appliance," filed Sep. 28, 2020, and which applications are incorporated by reference in their entireties. To the extent appropriate, a claim of priority is made to each of the above disclosed applications.

BACKGROUND

Sleep disorders, such as obstructive sleep apnea (OSA), are prevalent amongst the general population. If untreated, sleep disorders can increase the risk of various health problems, such as obesity, diabetes, cardiovascular disease, and depression. Oral appliance therapy is one example treatment for OSA. For example, an oral appliance device may be used to reposition a user's bite position such that the user's airway is kept open during sleep, thereby preventing the airway from collapsing and blocking the normal flow of air during breathing. While oral appliance devices can help to prevent airway blockages due at least in part to mandibular repositioning, current oral appliance devices do not stabilize the user's tongue in a non-obstructive position through sleep. As is known in the art, poor tongue positioning (sometimes also referred to as tongue posture) can additionally or alternatively cause OSA. For example, the tongue can easily and oftentimes fall back posteriorly when in a supine position and during sleep, which can cause an obstruction, particularly during REM (Rapid Eye Movement) and deep delta wave N3 stage sleep when muscles are paralyzed and atonic.

Accordingly, an apparatus is needed for providing oral appliance therapy and tongue stabilization. Also, while relatively specific problems have been discussed, it should be understood that the embodiments should not be limited to solving the specific problems identified in the background.

SUMMARY

The disclosure generally relates to an apparatus for providing tongue stabilization during oral appliance therapy. According to an aspect, the tongue stabilization apparatus can be integrated with or added to an oral appliance device. The tongue stabilization apparatus may be customizable to the user. For example, the tongue stabilization apparatus can be adjusted to the user's tongue size and/or shape and to the user's level of comfort and/or tolerance.

Accordingly, in one example, the present application describes a tongue stabilization apparatus, comprising: an upper clamp; a lower clamp; and a projection connected to at least one of the upper clamp and the lower clamp, wherein: actuation of the projection in a first direction causes at least one of the upper clamp and the lower clamp to be moved toward each other and grip a user's tongue; and actuation of the projection in an opposite direction causes at least one of the upper clamp and the lower clamp to be moved away from each other.

In another example, the present application describes an oral appliance device comprising a tongue stabilization apparatus, the tongue stabilization apparatus, comprising: an upper clamp; a lower clamp; and a projection connected to at least one of the upper clamp and the lower clamp, wherein: actuation of the projection in a first direction causes at least one of the upper clamp and the lower clamp to be moved toward each other and grip a user's tongue; and actuation of the projection in an opposite direction causes at least one of the upper clamp and the lower clamp to be moved away from each other.

In another example, the present application describes a method for stabilizing a user's tongue. In some examples, the method includes receiving a user's tongue between an upper clamp and a lower clamp of a tongue stabilization apparatus included in an oral appliance device; receiving an actuation of a projection connected to at least one of the upper clamp and the lower clamp, wherein: actuation of the projection in a first direction causes at least one of the upper clamp and the lower clamp to be moved toward each other and grip the user's tongue during use of the oral appliance device; and actuation of the projection in an opposite direction causes at least one of the upper clamp and the lower clamp to be moved away from each other.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

Non-limiting and non-exhaustive examples are described with reference to the following figures.

DETAILED DESCRIPTION

Figure 1A:
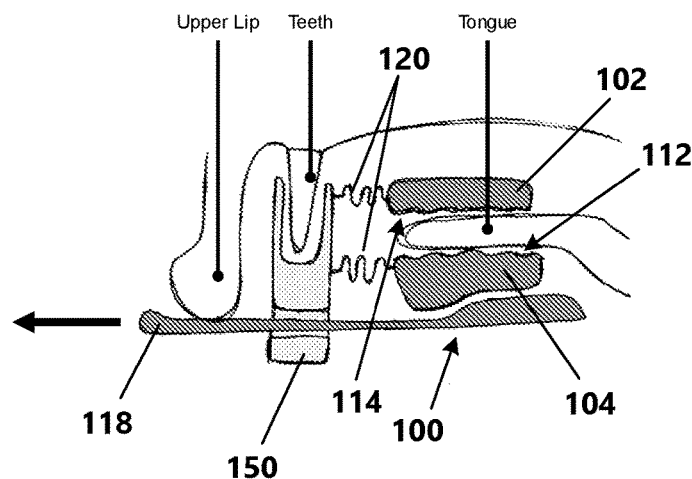
FIG. 1A is a side view illustration of an example tongue stabilization apparatus included in an example oral appliance device according to an embodiment.

The following detailed description refers to the accompanying drawings. Wherever possible, the same reference numbers are used in the drawings and the following description to refer to the same or similar elements. While aspects of the present disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the present disclosure, but instead, the proper scope of the present disclosure is defined by the appended claims. The following detailed description is, therefore, not to be taken in a limiting sense.

The present disclosure provides an apparatus for providing tongue stabilization during oral appliance therapy. The tongue stabilization apparatus is configured to hold a user's tongue in place or prohibit it from dropping back posteriorly, thereby stabilizing the user's tongue in a non-obstructive position through sleep, which can help to prevent the user from experiencing OSA. Example illustrations of an example tongue stabilization apparatus 100 are provided in FIGS. 1A-9. The tongue stabilization apparatus 100 can be built and assembled as a component that can be integrated into an oral appliance device 150 or added to an existing oral appliance device 150. The tongue stabilization apparatus 100 may be comprised of various materials that may be approved for use in a user's mouth during sleep. In some examples, the oral appliance device 150 (FIGS. 3-10) is a customized oral appliance device, such as one that is custom-fitted to the user by a dentist or other healthcare professional. For example, the customized oral appliance device may be an FDA-approved oral appliance device. One example oral appliance device 150 that can include the tongue stabilization apparatus 100 is an appliance, such as the therapeutic position verifying tool described in the patent application of Jerry C. Hu, Ser. No. 16/573,932 filed Sep. 17, 2019, which is hereby incorporated by reference in its entirety.

As mentioned above, the tongue stabilization apparatus 100 is configured to hold a user's tongue in place or prohibit it from dropping back posteriorly, thereby stabilizing the user's tongue in a non-obstructive position through sleep. For example, in myofunctional therapy, a goal is to position the tongue in the "N" spot (i.e., the position in a user's mouth where the user's tongue is placed when saying the letter "N"), where nasal breathing and other myofunctional goals may be maximized. According to an aspect, the tongue stabilization apparatus 100 is customizable to the user. For example, the tongue stabilization apparatus 100 can be adjusted to the user's tongue size and/or shape and to the user's level of comfort and/or tolerance.

The example tongue stabilization apparatus 100 includes at least one pair of an upper clamp 102 and a lower clamp 104. According to one aspect, the tongue stabilization apparatus 100 can be customized to a user. In one example, positioning of the at least one upper clamp 102 and lower clamp 104 on the user's tongue can be variable. In another example, different numbers of clamp pairs (e.g., a pair comprising an upper clamp 102 and a lower clamp 104) can be included in the tongue stabilization apparatus 100. The position and/or number of clamp pairs may be determined based on a size and/or shape of the user's tongue, arch, or other oral anatomy. The example tongue stabilization apparatus 100 illustrated in FIG. 1A includes one pair of the upper clamp 102 and the lower clamp 104; however, in other examples, additional clamp pairs (e.g., 2 clamp pairs, 3 clamp pairs, 4 clamp pairs) may be included. As an example, one user may have narrow arched oral anatomy with severe over closure and crowding, and accordingly, one clamp pair (102,104) in an anterior position may be used. As another example, another user with a high body mass index with and with macroglossia may require multiple clamp pairs (102, 104) positioned along the lateral dorsal borders of the user's tongue to provide better stabilization.

The upper clamp 102 and the lower clamp 104 are moveable between a tightened (clamped) position and a loosened (unclamped) position. When in the tightened/clamped position, the user's tongue is captured between an upper gripping surface 112 of the upper clamp 102 and a lower gripping surface 114 of the lower clamp 104 such that the user's tongue is securely held in a non-obstructive position through sleep. For example, the upper gripping surface 112 is in contact with a portion of the upper surface of the user's tongue, and the lower gripping surface 114 is in contact with a portion of the lower surface of the user's tongue. The upper gripping surface 112 and the lower gripping surface 114 can be made of a material that is operative to grip the user's tongue such that it is stabilized in a non-obstructive position but that is also acceptable to the user in terms of comfort. For example, the upper gripping surface 112 and the lower gripping surface 114 may be made of a rubber material, Polymethylmethacrylate (PMMA), or other material. In some examples, the upper gripping surface 112 and the lower gripping surface 114 are attached to the upper clamp 102 and the lower clamp 104, respectively. In other examples, the upper gripping surface 112 and the lower gripping surface 114 are formed integrally with the upper clamp 102 and the lower clamp 104, respectively.

Figure 1B:
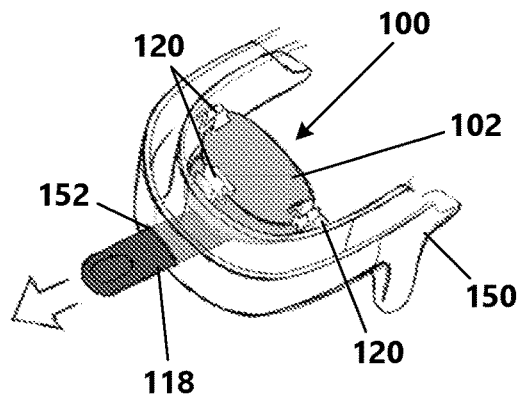
FIG. 1B is a front perspective view of the example tongue stabilization apparatus shown in FIG. 1A.
Figure 1C:
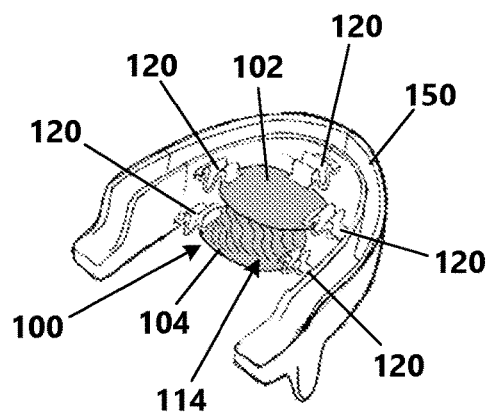
FIG. 1C is a rear perspective view of the example tongue stabilization apparatus shown in FIGS. 1A and 1B.

In some example aspects, movement of the upper clamp 102 and the lower clamp 104 is driven by actuation of a projection 118, wherein a first end of the projection 118 may be designed to project through or otherwise be located on a buccal or facial surface of an oral appliance device 150. In one example implementation, and as shown in FIGS. 1A, 1B, and 1C, a second end of the projection 118 may be designed to make contact with the bottom surface of the lower clamp 104. The second end of the projection 118 may be shaped such that movement of the projection 118 in an outward direction (i.e., away from the tongue stabilization apparatus 100 and the user's mouth) may cause the projection 118 to exert an upward force against the bottom surface of the lower clamp 104. The upper clamp 102, for example, may be limited in movement in the upward direction by the roof of the user's mouth. Thus, the lower clamp 104 may be pushed towards the upper clamp 102 and hold the user's tongue. As illustrated in FIGS. 1A, 1B, and 1C, in some examples, the upper clamp 102 and the lower clamp 104 may be connected to an oral appliance device 150 via a plurality of springs 120, which may allow for limited movement of the user's tongue. The springs 120, for example and as best shown in FIGS. 1B and 1C, may include a plurality of springs 120 to the oral appliance device 150 and the upper clamp 102. Additionally, a plurality of springs 120 may be attached between the oral appliance device 150 and the lower clamp 104. In some examples, the projection 118 may be held in position via a friction fit. In other examples, the projection 118 may be held in position via a ratcheting mechanism. The ratcheting mechanism, for example, can be implemented in the tongue stabilization apparatus 100 or in the oral appliance device 150.

Figure 2:
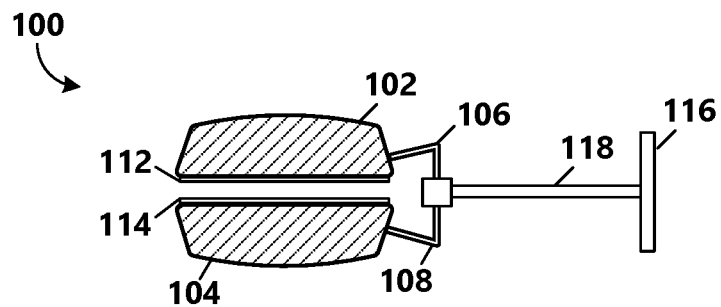
FIG. 2 is a side view illustration of an example tongue stabilization apparatus according to an embodiment.
Figure 3:
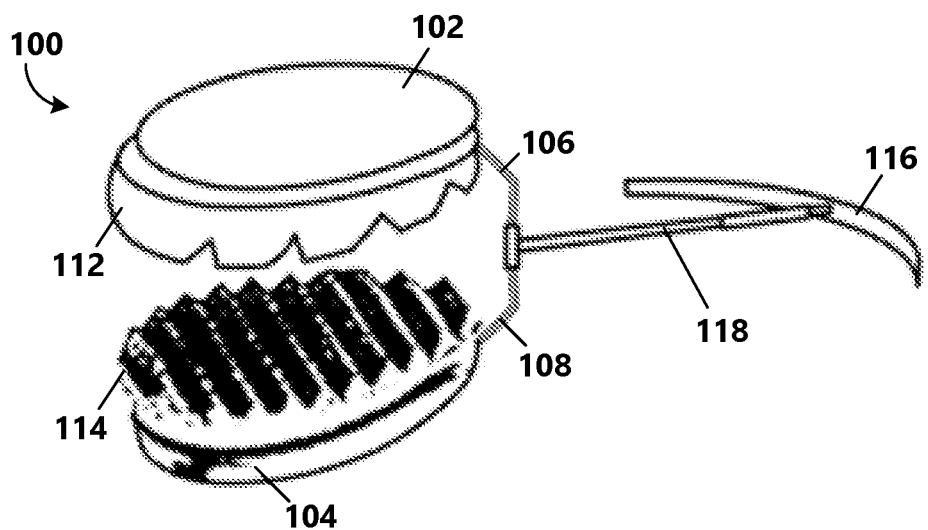
FIG. 3 is a rear profile view illustration of the example tongue stabilization apparatus shown in FIG. 2 according to an embodiment.
Figure 4:
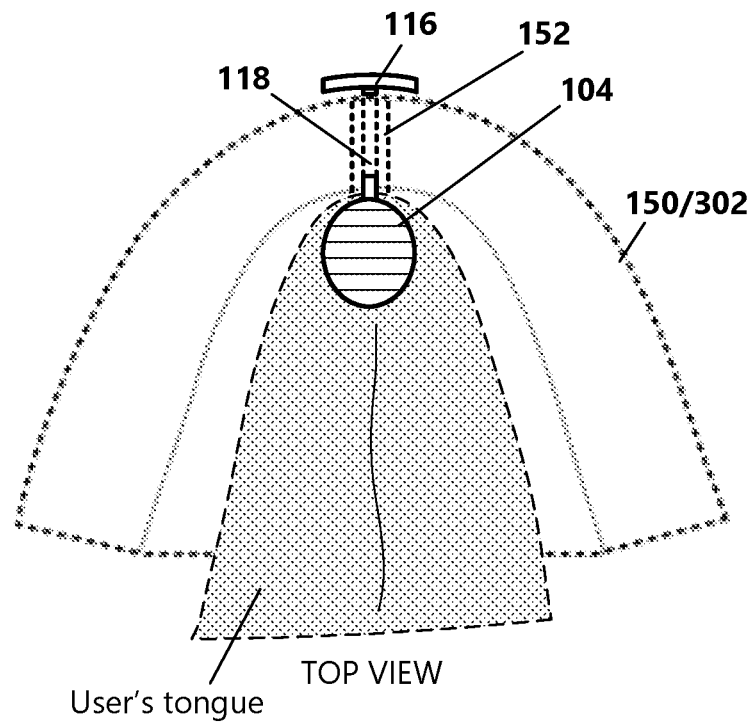
FIG. 4 is a top view illustration of an example tongue stabilization apparatus included in an example oral appliance device and positioned on a user's tongue according to an embodiment.
Figure 5:
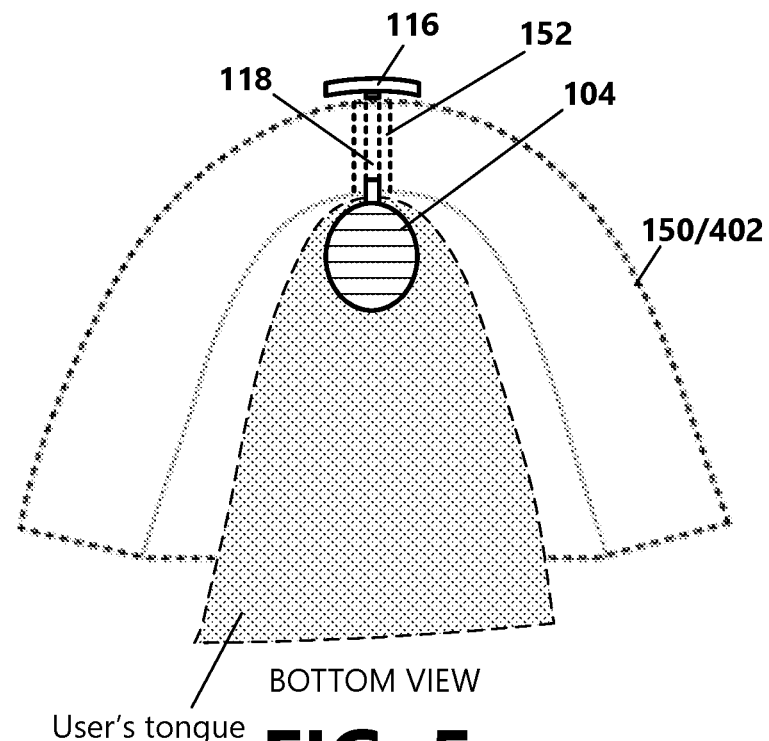
FIG. 5 is a bottom view illustration of the example tongue stabilization apparatus shown in FIG. 4 according to an embodiment.
Figure 6:
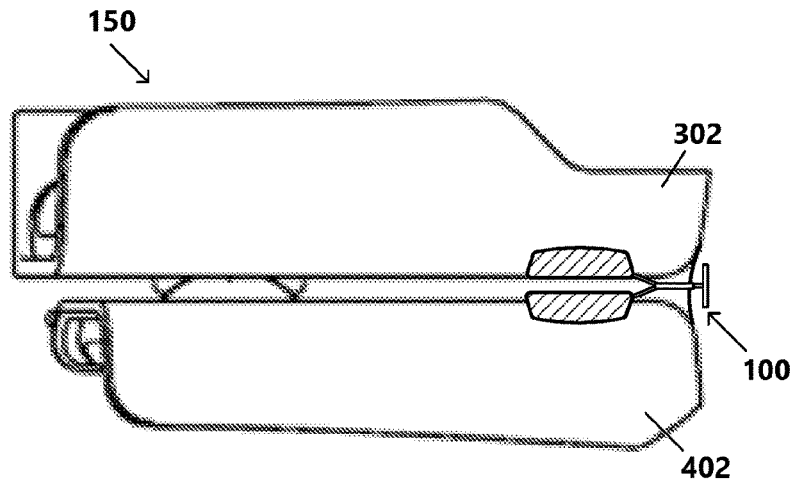
FIG. 6 is a side view illustration of the example tongue stabilization apparatus included in an example oral appliance device according to an embodiment.
Figure 7:
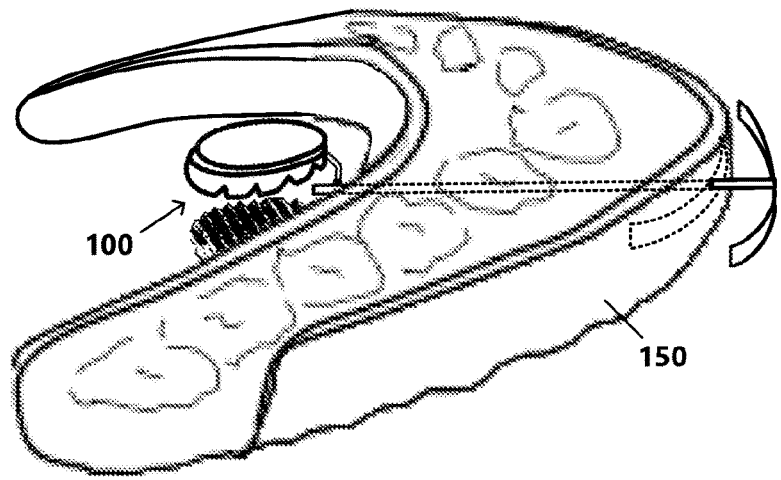
FIG. 7 is a side profile view illustration of the example tongue stabilization apparatus included in an example oral appliance device according to an embodiment.
Figure 8:
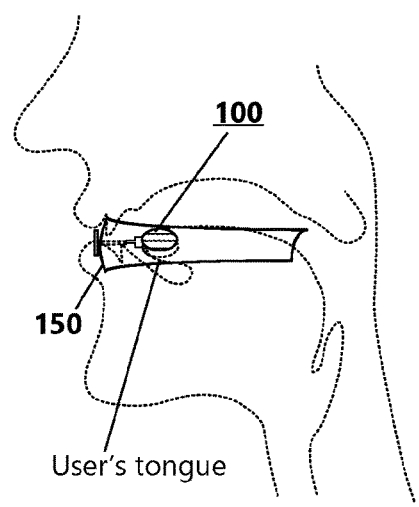
FIG. 8 is an illustration of an example oral appliance device including an example tongue stabilization apparatus shown worn by a user.

In another example implementation, and as shown in FIGS. 2-9C, the projection 118 may comprise an adjustment mechanism 116. According to an example, the projection 118 may be designed to extend through an opening 152 defined in the oral appliance device 150, and the adjustment mechanism 116 may be located at the first end of the projection 118. For example, the adjustment mechanism 116 may be designed to be actuated by the user, such as to tighten and loosen the upper clamp 102 and/or lower clamp 104. FIG. 2 shows a side view of an example tongue stabilization apparatus 100 comprising the adjustment mechanism 116 and FIG. 3 is a perspective view of another example stabilization apparatus 100 comprising the adjustment mechanism 116. Additionally, FIGS. 4 and 5 show a top and bottom view, respectively, of an example tongue stabilization apparatus 100 comprising the adjustment mechanism 116 that may operate to adjust one or both of the upper clamp 102 and the lower clamp 104 to hold the user's tongue in place or to prohibit the user's tongue from dropping back posteriorly, such as during sleep.

In one example, and as best shown in FIGS. 2 and 3, the second end of the projection 118 may be configured to attach to an upper clamp arm 106 extending from the upper clamp 102 and/or a lower clamp arm 108 extending from the lower clamp 104. In another example, one or more cables may be configured to attach to the adjustment mechanism 116, extend through a channel defined through the projection 118, and extend through the second end of the projection 118 to attach to one or both clamp arm(s) 106,108 for enabling the adjustment mechanism 116 to tighten and loosen the tongue stabilization apparatus 100. In another example, the upper clamp arm 106 and/or the lower clamp arm 108 may be configured as cables or wires that are designed to attach to and be adjusted by the adjustment mechanism 116 of the projection 118. The projection 118, upper clamp 102, lower clamp 104, adjustment mechanism 116, upper clamp arm 106, lower clamp arm 108, and/or cables/wires may be made of various types and combinations of materials (e.g., PMMA, ceramic, metal, non-metal).

According to various examples, the adjustment mechanism 116 is configured to be actuated by a user, such that actuation of the adjustment mechanism 116 in a first direction causes one or both of the upper clamp 102 and the lower clamp 104 to be moved toward each other, and actuation of the projection 118 in the opposite direction from the first direction causes one or both of the upper clamp 102 and the lower clamp 104 to move away from each other. When the upper clamp 102 and the lower clamp 104 are moved toward each other, the tongue stabilization apparatus 100 is in a tightened (clamped) position, and when the upper clamp 102 and the lower clamp 104 are moved away from each other, the tongue stabilization apparatus 100 is in a loosened (unclamped) position. Movement of the upper clamp 102 and/or the lower clamp 104 in response to actuation of the adjustment mechanism 116 can be implemented via various methods and using one or a combination of tightening and/or loosening mechanisms.

Figure 9A:
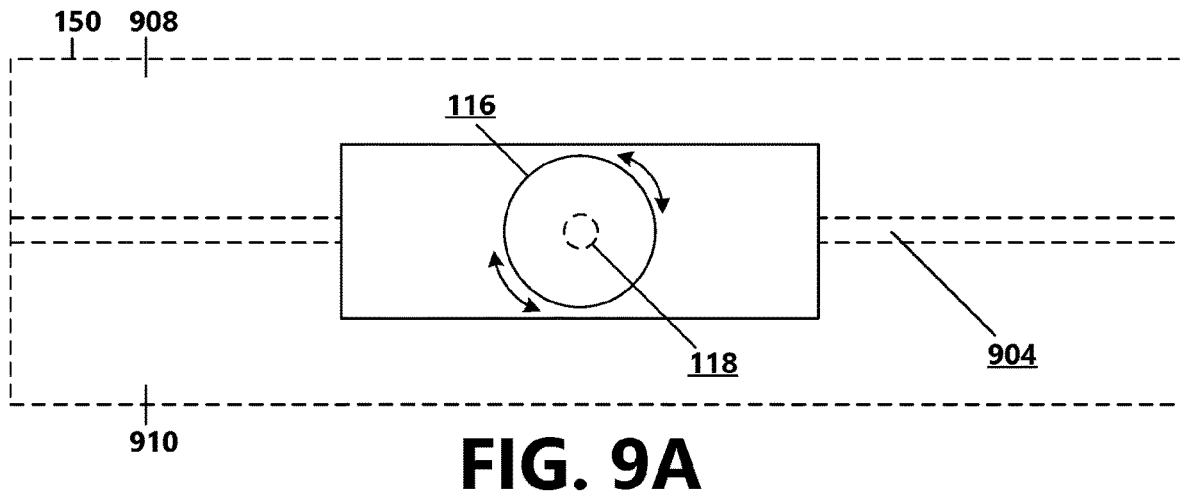
FIGS. 9A-C are illustrations of example clamp adjustment designs and configurations according to an embodiment.
Figure 9B:
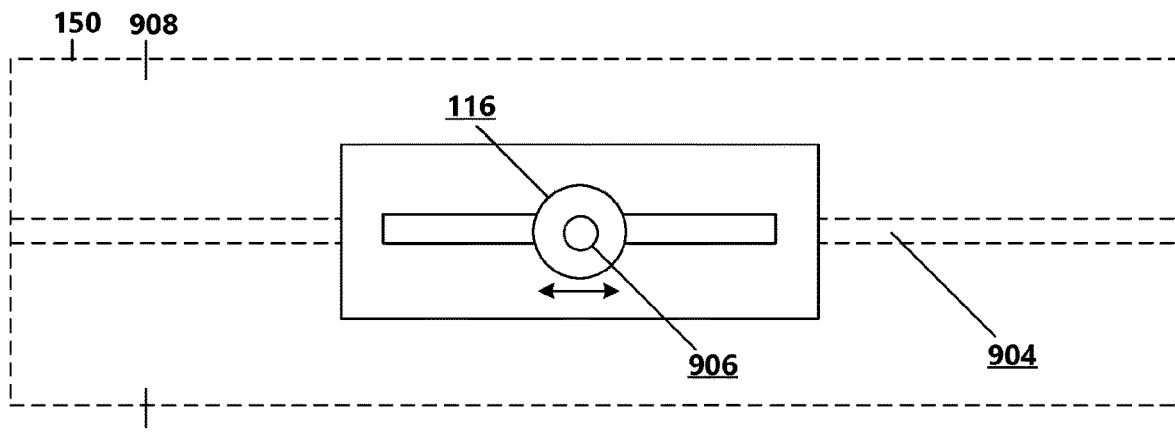
Figure 9C:
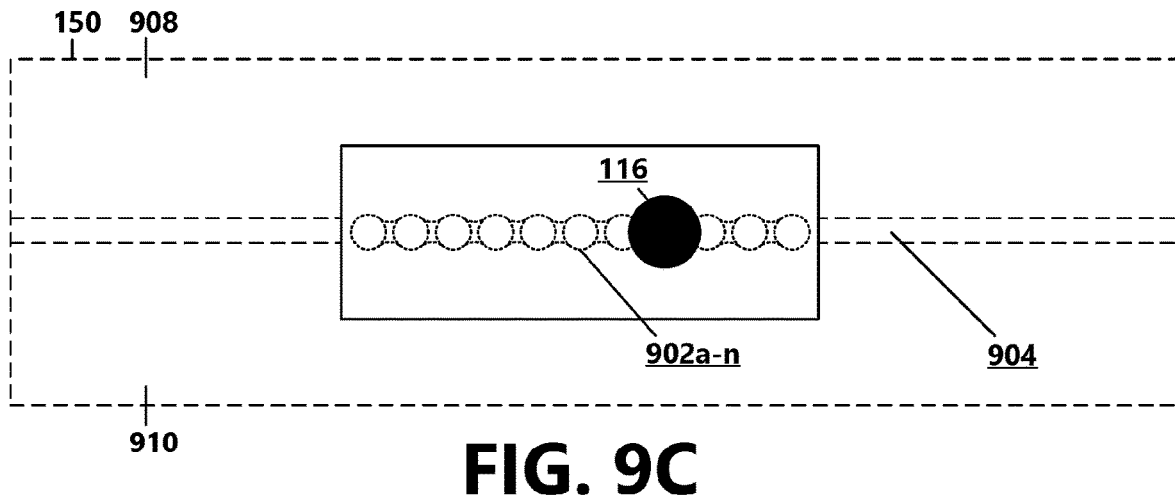

Various non-limiting example projection 118 and adjustment mechanism 116 designs and configurations are shown in FIGS. 9A-C. FIG. 9A shows a front view of an oral appliance device 150 including a projection 118 comprising an example adjustment mechanism 116. The example adjustment mechanism 116 may be designed to be rotated in a first direction (e.g., a clockwise or counter-clockwise direction) to move one or both of the upper clamp 102 and the lower clamp 104 toward each other, and to be rotated in a second direction opposite the first direction to move one or both of the upper clamp 102 and the lower clamp 104 away from each other. In some examples, the adjustment mechanism 116 can be pulled outward away from the oral appliance device 150 to unlock and rotate the adjustment mechanism 116, and can be pushed inward toward the oral appliance device 150 to lock and prevent rotation of the adjustment mechanism 116.

FIG. 9B shows an example adjustment mechanism 116 integrated in or attached to an oral appliance device 150. The example adjustment mechanism 116 may be designed to slide in a left and right direction. For example, sliding the adjustment mechanism 116 in one direction may cause one or both of the upper clamp 102 and the lower clamp 104 to be biased toward each other, and sliding the adjustment mechanism 116 in the opposite direction may cause one or both of the upper clamp 102 and the lower clamp 104 to be biased away from each other. According to an example, when the desired tongue clamping is attained by sliding the adjustment mechanism 116 until the user's tongue is held by the upper clamp 102 and the lower clamp 104 in a secure and comfortable state, the adjustment mechanism 116 can be pushed inward to a locked position or a button 906 located on the adjustment mechanism 116 can be pushed such that the adjustment mechanism 116 is placed into a locked position where it cannot be slid left or right and the upper clamp 102 and the lower clamp 104 are in a locked state. In one example, to unlock the adjustment mechanism 116 (and clamp(s) 102,104), the adjustment mechanism 116 may be pulled in an outward direction away from the oral appliance device 150 to an unlocked position where it can be moved from left or right and the upper clamp 102 and/or the lower clamp 104 are adjusted accordingly. In another example, the button 906 may be pushed in to place the adjustment mechanism 116 into an unlocked state.

FIG. 9C shows an example adjustment mechanism 116 designed to be pulled outward away from the oral appliance device 150 to move one or both of the upper clamp 102 and the lower clamp 104 away from each other, such as to insert the user's tongue between the upper clamp 102 and the lower clamp 104. For example, one or both of the upper clamp 102 and the lower clamp 104 may normally be in a clamped position. When the adjustment mechanism 116 is moved into one of a plurality of locking positions 902a-n (generally 902), the tongue stabilization apparatus 100 may be in one of a plurality of clamping positions. For example, each locking position 902 may correspond with a clamping position, wherein each clamping position may adjust an amount of force that may be exerted on the user's tongue between the upper clamp 102 and the lower clamp 104. In one example, pulling the adjustment mechanism 116 may move one or both of the clamp arms 112,114, and thus one or both of the clamps 102,104 away from each other. Or, in another example, one or both of the upper clamp 102 and the lower clamp 104 may normally be in a clamped position, and the clamp arms 112,114 may be embodied as cables or wires attached to the adjustment mechanism 116, such that when the adjustment mechanism 116 is pulled outward by the user, one or both of the upper clamp arm 112 and the lower clamp arm 114 may move one or both of the clamps 102,104 away from each other. When the upper clamp 102 and the lower clamp 104 are positioned on the user's tongue correctly, the user can release the adjustment mechanism 116 or move the adjustment mechanism 116 into a locking position 802 to maintain the upper clamp 102 and the lower clamp 104 in place.

As mentioned above, an opening 152 may be defined in the oral appliance device 150 through which the projection 118 may be designed to extend. When the tongue stabilization apparatus 100 is integrated into an oral appliance device 150, the opening 152 may be formed as part of forming the oral appliance device 150. Alternatively, when the tongue stabilization apparatus 100 is added to an existing oral appliance device 150, the opening 152 may be drilled into the oral appliance device 150, and the projection 118 may then be extended through the opening 152. In some examples, the opening 152 is defined in the oral appliance device 150 in a middle section 904 positioned between an upper arch 908 for holding the user's upper teeth and a lower arch 910 for holding the user's lower teeth. In some embodiments, the upper arch 908 and the lower arch 910 may be a single assembly. In some embodiments, the upper arch upper arch 908 and the lower arch 910 may be separate pieces that are connected together by the middle section 904. According to an aspect, the oral appliance device 150 may allow for the upper arch 908 and lower arch 910 to slide/move during the individual's sleep. In some examples, one or more fins or wings may be included as part of the oral appliance device 150. For example, the size and thickness of the wings may limit the amount of lateral excursion the user's mandible can move when the user is wearing the oral appliance device 150.

Figure 10A:
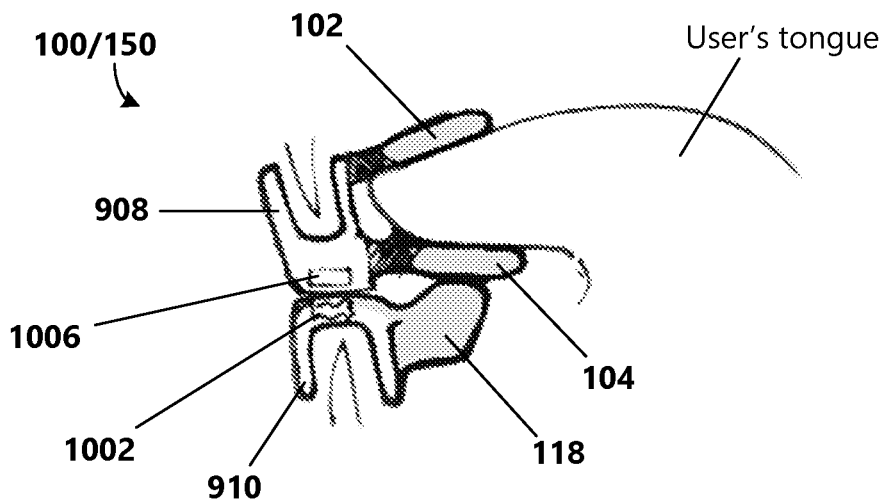
FIG. 10A is a side view illustration of an example tongue stabilization apparatus included in an example oral appliance device according to an embodiment.
Figure 10B:
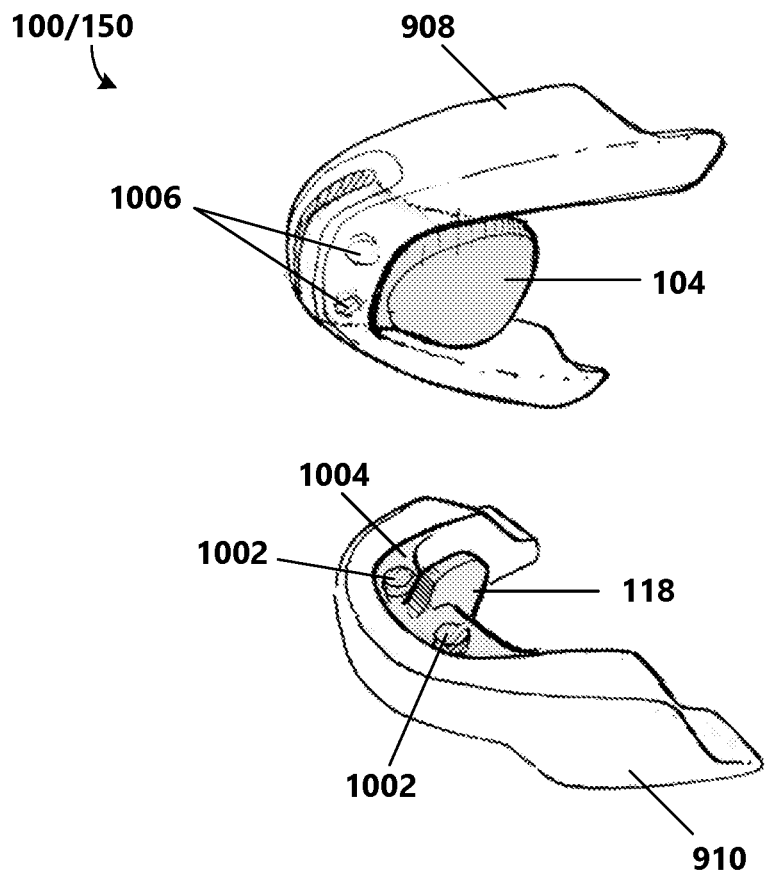
FIG. 10B is a front side perspective view of the example tongue stabilization apparatus shown in FIG. 10A.

Another example implementation of a tongue stabilization apparatus 100 is shown in FIGS. 10A and 10B. For example, FIG. 10A is a side view illustration of an example tongue stabilization apparatus 100 that may be formed as part of or added to an oral appliance device 150 according to an embodiment, and FIG. 10B is a front side perspective view of the example tongue stabilization apparatus shown in FIG. 10A. According to an example, the oral appliance device 150 may be comprised of a separate upper arch 908 and lower arch 910. As best shown in FIG. 10A, the top clamp 102 and the bottom clamp 104 may both be attached to the upper arch 908, and the projection 118 may be attached to the lower arch 910. The projection 118, in this example, may be shaped and designed to contact and exert an upward force against the bottom surface of the lower clamp 104 when the tongue stabilization apparatus 100 is in a clamped position. In this example, a clamped position may be achieved when the upper arch 908 and the lower arch 910 of the oral appliance device 150 are in contact. For example, movement of the upper arch 908 and the lower arch 910 toward each other (e.g., toward a biting position) may cause the projection 118 to exert an upward force against the bottom surface of the lower clamp 104. The upward force may cause the lower clamp 104 to be moved towards upper clamp 102 and hold the user's tongue. For example, the top clamp 102 may be attached to the upper arch 908 more rigidly than the bottom clamp 104, allowing the top clamp 102 and the bottom clamp 104 to hold the user's tongue securely based on the upward force of the projection 118 against the lower clamp 104.

In some examples, the projection 118 may be attached to the lower arch 910 of the oral appliance device 150 via a platform 1004. For example, the platform 1004 may be configured to attach to the oral appliance device 150. In some examples, positioning of the projection 118 on the oral appliance device 150 is adjustable (e.g., left/right, up/down). As best shown in FIG. 10B, the platform 1004 may comprise one or more magnets 1002, which may be configured to exert an attractive force on one or more other magnets 1006 (or other attractive material) located in the upper arch 908. For example, the magnets 1002,1006 may help to secure the upper arch 908 and bottom arch 910 in place, and thus, secure the user's tongue between the top clamp 102 and the bottom clamp 104 of the tongue stabilization apparatus 100.

Other means for moving one or both of the clamps 102,104 between the clamped and unclamped positions are possible and are within the scope of the present disclosure.

The description and illustration of one or more aspects provided in this application are intended to provide a thorough and complete disclosure of the full scope of the subject matter to those skilled in the art and are not intended to limit or restrict the scope of the invention as claimed in any way. The aspects, examples, and details provided in this application are considered sufficient to convey possession and enable those skilled in the art to practice the best mode of the claimed invention. Descriptions of structures, resources, operations, and acts considered well-known to those skilled in the art may be brief or omitted to avoid obscuring lesser known or unique aspects of the subject matter of this application. The claimed invention should not be construed as being limited to any embodiment, aspects, example, or detail provided in this application unless expressly stated herein. Regardless of whether shown or described collectively or separately, the various features (both structural and methodological) are intended to be selectively included or omitted to produce an embodiment with a particular set of features. Further, any or all of the functions and acts shown or described may be performed in any order or concurrently. Having been provided with the description and illustration of the present application, one skilled in the art may envision variations, modifications, and alternate embodiments falling within the spirit of the broader aspects of the general inventive concept provided in this application that do not depart from the broader scope of the present disclosure.

I claim:

1. A tongue stabilization apparatus, comprising:
an upper clamp;
a lower clamp; and
a projection connected to at least one of the upper clamp and the lower clamp, wherein:
actuation of the projection in a first direction causes at least a first one of the upper clamp and the lower clamp to be moved toward a second one of the upper clamp and the lower clamp, and the upper claim and the lower clamp are configured to grip a user's tongue in response to actuation of the projection in the first direction; and
actuation of the projection in an opposite direction causes at least the first one of the upper clamp and the lower clamp to be moved away from the second one of the upper clamp and the lower clamp.

2. The tongue stabilization apparatus of claim 1, wherein the actuation is a pulling force exerted on the projection.

3. The tongue stabilization apparatus of claim 1, wherein the projection comprises an adjustment mechanism.

4. The tongue stabilization apparatus of claim 3, wherein rotation of the adjustment mechanism in the first direction causes at least the first one of the upper clamp and the lower clamp to be moved toward the second one of the upper clamp and the lower clamp, and rotation of the adjustment mechanism in the opposite direction causes at least the first one of the upper clamp and the lower clamp to be moved away from the second one of the upper clamp and the lower clamp.

5. The tongue stabilization apparatus of claim 1, wherein the tongue stabilization apparatus is attached to or integrated into an oral appliance device.

6. The tongue stabilization apparatus of claim 5, wherein:
a first end of the projection extends through an opening defined in the oral appliance device;
a second end of the projection is in contact with a bottom surface of the lower clamp; and
a pulling force exerted on the projection causes the second end of the projection to exert and upward force on the bottom surface of the lower clamp to grip the user's tongue.

7. The tongue stabilization apparatus of claim 6, wherein the upper clamp and the lower clamp are attached to the oral appliance device via a plurality of springs.

8. The tongue stabilization apparatus of claim 6, wherein the projection is held in place via a ratcheting mechanism.

9. The tongue stabilization apparatus of claim 5, wherein:
the oral appliance device comprises an upper arch for holding the user's top teeth and a lower arch for holding the user's bottom teeth;
the upper clamp and the lower clamp are attached to the upper arch;
a first end of the projection is attached to the lower arch;
a second end of the projection is designed to exert an upward force on a bottom surface of the lower clamp when the upper arch and the lower arch are in contact; and
the upward force causes the lower clamp to move toward the upper clamp to grip the user's tongue.

10. The tongue stabilization apparatus of claim 9, wherein:
the upper arch comprises one or more magnets;
the first end of the projection is attached to the lower arch via a platform; and
the platform comprises one or more magnets that operate to exert an attractive force on the one or more magnets in the upper arch to secure the grip on the user's tongue.

11. The tongue stabilization apparatus of claim 10, wherein the platform is adjustable.

12. An oral appliance device comprising a tongue stabilization apparatus, the tongue stabilization apparatus, comprising:
an upper clamp;
a lower clamp; and
a projection connected to at least one of the upper clamp and the lower clamp, wherein:
actuation of the projection in a first direction causes at least a first one of the upper clamp and the lower clamp to be moved toward a second one of the upper clamp and the lower clamp, and the upper clamp and the lower clamp are configured to grip a user's tongue in response to actuation of the projection in the first direction; and
actuation of the projection in an opposite direction causes at least the first one of the upper clamp and the lower clamp to be moved away from the second one of the upper clamp and the lower clamp.

13. The oral appliance device of claim 12, wherein the actuation is a pulling force exerted on the projection.

14. The oral appliance device of claim 12, wherein the projection comprises an adjustment mechanism, wherein rotation of the adjustment mechanism in the first direction causes at least the first one of the upper clamp and the lower clamp to be moved toward the second one of the upper clamp and the lower clamp, and rotation of the adjustment mechanism in the opposite direction causes at least the first one of the upper clamp and the lower clamp to be moved away from the second one of the upper clamp and the lower clamp.

15. The oral appliance device of claim 12, wherein
a first end of the projection extends through an opening defined in the oral appliance device;
a second end of the projection is in contact with a bottom surface of the lower clamp; and
a pulling force exerted on the projection causes the second end of the projection to exert and upward force on the bottom surface of the lower clamp to grip the user's tongue.

16. The oral appliance device of claim 15, wherein the upper clamp and the lower clamp are attached to the oral appliance device via a plurality of springs.

17. The oral appliance device of claim 15, wherein:
the oral appliance device comprises an upper arch for holding the user's top teeth and a lower arch for holding the user's bottom teeth;
the upper clamp and the lower clamp are attached to the upper arch;
a first end of the projection is attached to the lower arch;
a second end of the projection is designed to exert an upward force on a bottom surface of the lower clamp when the upper arch and the lower arch are in contact; and
the upward force causes the lower clamp to move toward the upper clamp to grip the user's tongue.

18. The oral appliance device of claim 17, wherein:
the upper arch comprises one or more magnets;
the first end of the projection is attached to the lower arch via a platform; and
the platform comprises one or more magnets that operate to exert an attractive force on the one or more magnets in the upper arch to secure the grip on the user's tongue.

19. The oral appliance device of claim 18, wherein the platform is adjustable.

20. A method for stabilizing a user's tongue, comprising:
receiving a user's tongue between an upper clamp and a lower clamp of a tongue stabilization apparatus included in an oral appliance device;
receiving an actuation of a projection connected to at least one of the upper clamp and the lower clamp, wherein:
actuation of the projection in a first direction causes at least a first one of the upper clamp and the lower clamp to be moved toward a second one of the upper clamp and the lower clamp and causes the upper clamp and the lower clamp to grip the user's tongue during use of the oral appliance device; and
actuation of the projection in an opposite direction causes at least the first one of the upper clamp and the lower clamp to be moved away from the second one of the upper clamp and the lower clamp.

* * * * *